(12) United States Patent
Medford et al.

(10) Patent No.: US 6,713,621 B1
(45) Date of Patent: Mar. 30, 2004

(54) CHIMERIC OLIGONUCLEOTIDES FOR MODULATING GENE EXPRESSION

(75) Inventors: Russell M. Medford, Atlanta, GA (US); Clarence Frank Bennett, Carlsbad, CA (US)

(73) Assignees: ISIS Pharmaceuticals, Inc., Carlsbad, CA (US); Emory University, Atlanta, GA (US)

( * ) Notice: Subject to any disclaimer, the term of this patent is extended or adjusted under 35 U.S.C. 154(b) by 1,025 days.

(21) Appl. No.: 08/401,192

(22) Filed: Mar. 9, 1995

Related U.S. Application Data

(62) Division of application No. 08/147,878, filed on Nov. 5, 1993, now Pat. No. 6,399,376.

(51) Int. Cl.$^7$ .......................... C07H 21/02; C07H 21/04; A01N 43/04; A61K 31/70

(52) U.S. Cl. .......................... 536/24.5; 536/23.1; 514/44

(58) Field of Search .............................. 536/24.5, 23.1, 536/23.5; 514/44; 424/93.2; 435/69.1, 320.1, 325, 375, 455

(56) References Cited

U.S. PATENT DOCUMENTS

| | | | |
|---|---|---|---|
| 5,034,506 A | 7/1991 | Summerton et al. | 528/391 |
| 5,098,890 A | 3/1992 | Gewirtz et al. | 514/44 |
| 5,157,115 A | 10/1992 | Taniguchi | 536/27 |
| 5,166,195 A | 11/1992 | Ecker | 514/44 |

FOREIGN PATENT DOCUMENTS

| | | |
|---|---|---|
| EP | 0 331 939 A2 | 9/1989 |
| WO | WO 91/11535 | 8/1991 |
| WO | WO 91/14790 | 10/1991 |
| WO | WO 91/15114 | 10/1991 |
| WO | WO 92/03139 | 3/1992 |
| WO | WO 92/18522 | 10/1992 |
| WO | WO 92/19732 | 11/1992 |
| WO | WO 93/18052 | 9/1993 |

OTHER PUBLICATIONS

C Helene et al (1990) Biochimica et Biophysica Acta 1049:99–125.*

H lnove et al (1987) FEBS Letters 215:327–330.*

PCT Supplementary Partial European Search Report dated Dec. 11, 1998, 7 pages.

Medford, R.M. et al., "Inhibition of TNFα Induced Vascular Cell Adhesion Molecule–1 Gene Expression in Human Vascular Endothelial and Smooth Muscle Cells Using Transcriptional Factor Decoys", *Circulation*, Oct. 1993, p. I–77, Abstract 0401.

Androphy et al, "Bovine papillomavirus E2 trans–activating gene product binds to specific sites in papillomavirus DNA," *Nature* 325:70–73, 1987.

Bevilacqua et al., "Identification of an inducible endothelial–leukocyte adhesion molecule," *Proc. Natl. Acad. Sci. USA* 84:9238–9242, 1987.

Bevilacqua et al., "Endothelial Leukocyte Adhesion Molecule 1: An Inducible Receptor for Neutrophils Related to Complement Regulatory Proteins and Lectins," *Science* 243:1160–1165, 1989.

Bielinska et al., "Regulation of Gene Expression with Double–Stranded Phosphorothioate Oligonucleotides," *Science* 250;997–1000, 1990.

Campbell et al., "Intercellular adhesion molecule 1 is induced on isolated endocrine islet cells by cytokines but not by reovirus infection," *Proc. Natl. Acad. Sci. U.S.A.* 86:4282–4286, 1989.

Chu et al. "Binding of Hairpin and Dumbbell DNA to Transcription Factors", *Nucleic Acids Research* 19:6958, 1991.

Clusel et al., "Ex vivo regulation of specific gene expression by nanomolar concentration of double–stranded dumbbell oligonucleotides," *Nucleic Acids Research* 21:3405–3411, 1993.

Collins et al., "Structure and Chromosomal Location of the Gene for Endothelial Leukocyte Adhesion Molecule 1," *J. Biol. Chem.* 266:2466–2473, 1991.

Cornelius et al., "A 5' Portion of the ICAM–1 Gene Confers Tissue–Specific Differential Expression Levels and Cytokine Responsiveness," *J. of Investigative Dermatology* 100:753–758, 1993.

Cosimi et al., "In Vivo Effects of Monoclonal Antibody to ICAM–1 (CD54) In Nonhuman Primates with Renal Allografts," *J. Immunol.* 144:4604–4612, 1990.

Degitz et al., "Cloning and Characterization of the 5'–Transcriptional Regulatory Region of the Human Intercellular Adhesion Molecule I Gene," *J. of Biological Chemistry* 266:14024–14030, 1991.

Dustin and Springer, "Lymphocyte Function–associated Antigen–1 (LFA–1) Interaction with Intercellular Adhesion Molecule–1 (ICAM–1) is One of At Least Three Mechanisms for Lymphocyte Adhesion to Cultured Endothelial Cells," *J. Cell Biol.* 107:321–331, 1988.

Eck et al., "Inhibition of Phorbol Ester–Induced Cellular Adhesion by Competitive Binding of NF–κB In Vivo," *Molecular and Cellular Biol.* 13:6530–6536, 1993.

(List continued on next page.)

Primary Examiner—Scott D. Priebe
Assistant Examiner—Sumesh Kaushal
(74) Attorney, Agent, or Firm—Woodcock Washburn LLP

(57) ABSTRACT

Genes coding for vascular cell adhesion molecules, particularly VCAM–1, are modulated through interaction of oligonucleotides with transcriptional regulatory factors which bind to the genes. Specific and effective oligonucleotides are provided which interact with the transcriptional regulatory factors to diminish their interaction with the genes and downregulate their function. Multi-modal oligonucleotides are also provided which interact both with a transcriptional regulatory factor and with another aspect of gene function.

9 Claims, No Drawings-

OTHER PUBLICATIONS

Faull and Russ, "Tubular Expression of Intercellular Adhesion Molecule–1 During Renal Allograft Rejection," *Transplantation* 48: 226–230, 1989.

Frohman et al., "The induction of intercellular adhesion molecule 1 (ICAM–1) expression on human fetal astrocytes by interferon–γ, tumor necrosis factor α, lymphotoxin, and interleukin–1: relevance to intracerebral antigen presentation," *J. Neuroimmunol.* 23:117–124.

Greve et al., "The Major Human Rhinovirus Receptor is ICAM–1," *Cell* 56:839–847, 1989.

Griffiths and Nickoloff, Keratinocyte Intercellular Adhesion Molecule–1 (ICAM–1) Expression Precedes Dermal T Lymphocytic Infiltration in Allergic Contact Dermatitis (*Rhus dermatitis*) *Am. J. Pathology* 135:1045–1053, 1989.

Hale et al., "Immunohistologic Analysis of the Distribution of Cell Adhesion Molecules within the Inflammatory Synovial Microenvironment," *Arthritis and Rhuematism* 32:22–30, 1989.

Harlan, J.M., "Leukocyte–Endothelial Interactions," *Blood* 65:513–525, 1985.

Hayashi et al. "Oxidoreductive Regulation of Nuclear Factorκ B," *J. Biol. Chem.* 268:11380–11388, 1993.

Ho et al., "Treatment of severe lichen planus with cyclosporine," *J. Am. Acad. Dermatol.* 22:64–68, 1990.

Hooft van Huijsduijnen et al., "A T–cell Enhancer Cooperates with NF–κB to Yield Cytokine Induction of E–selection Gene Transcription in Endothelial Cells," *J. Biol. Chem.* 267:22385–22391, 1992.

Iademarco et al., Characterization of the Promoter for Vascular Cell Adhesion Molecule–1 (VCAM–1) *J. Biol. Chem.* 267:16323–16329, 1992.

Libby et al., "Vascular Cell Adhesion Molecule–1 and Smooth Muscle Cell Activation During Atherogenesis," *J. Clin. Invest.* 92:538–539, 1993.

Lisby et al., "Intercellular adhesion molecule–I (ICAM–I) expression correlated to inflammation," *British Journal Dermatol.* 120:479–484, 1989.

Marlin et al., "A soluble form of intercellular adhesion molecule–1 inhibits rhinovirus infection," *Nature* 344:70–72, 1990.

Morimoto, R.I., "Transcription Factors: Positive and Negative Regulators of Cell Growth and Disease," *Current Opinion in Cell Biology* 4: 480–487, 1992.

Nielsen et al., "Sequence–Selective Recognition of DNA by Strand Displacement with a Thymine–Substituted Polyamide," *Science* 254:1497–1500, 1991.

O'Brien et al., "Vascular Cell Adhesion Molecule–1 Is Expressed in Human Coronary Atheroscierotic Plaques," *J. Clin. Invest.* 92:945–951, 1993.

Osborn et al., Direct Expression Cloning of Vascular Cell Adhesion Molecule 1, a Cytokine–Induced Endothelial Protein That Binds to Lymphocytes, *Cell* 59:1203–1211, 1989.

Pabo and Sauer, "Transcription factors: Structural Families and Principles of DNA Recognition," *Annu. Rev. Biochem.* 61:1053–1095, 1992.

Rice and Bevilacqua, "An Inducible Endothelial Cell Surface Glycoprotein Mediates Melanoma Adhesion," *Science* 246:1303–1306, 1989.

Rice et al., "Inducible Cell Adhesion Molecule 110 (INCAM–110) Is an Endothelial Receptor For Lymphocytes," *J. Exp. Med.* 171:1369–1374, 1990.

Sen et al., "Multiple Nuclear Factors Interact with the Immunoglobulin Enhancer Sequences," *Cell* 46: 705–716, 1986.

Shiohara et al., "Fixed Drug Eruption," *Arch. Dermatol.* 125:1371–1376, 1989.

Staunton et al., "Primary Structure of ICAM–1 Demonstrates Interaction between Members of the Immunoglobulin and Integrin Supergene Families," *Cell* 52:925–933, 1988.

Staunton et al., "A Cell Adhesion Molecule, ICAM–1, Is the Major Surface Receptor for Rhinoviruses," *Cell* 56:849–853, 1989.

Staunton et al., "The Arrangement of the Immunoglobin–like Domains of ICAM–1 and the Binding Sites for LFA–1 and Rhinovirus," *Cell* 61: 243–254, 1990.

Voraberger et al., "Cloning of the Human Gene for Intercellular Adhesion Molecule 1 and Analysis of its 5' –Regulatory Region," *J. of Immunology* 147:2777–2786, 1991.

Weetman et al., "Expression of an intercellular adhesion molecule, ICAM–1, by human thyroid cells," *J. Endocrinol.* 122:185–191, 1989.

Wegner et al., "Intercellular Adhesion Molecule–1 (ICAM–1) in the Pathogenesis of Asthma," *Science* 247:456–459, 1990.

Wellicome et al., "A monoclonal antibody that Detects a Novel Antigen on Endothelial Cells that is Induced by Tumor Necrosis Factor, IL–1, or Lipopolysaccharide," *J. Immunol.* 144:2558–2565, 1990.

Wu, et al. "Inhibition of in Vitro Transcription by Specific Double–Stranded Oligodeoxyribonucleotides," *Gene* 89:203–209, 1990.

Adams et al., "Intercellular Adhesion Molecule 1 on Liver Allografts During Rejection," *Lancet* pp. 1122–1125, 1989.

Cybulsky, M., "Gene Structure, Chromosomal Location, and Basis for Alternative mRNA Splicing of the Human VCAM1 Gene", *PNAS USA* 1991, 988, 7859–7863.

Neish et al., "Functional Analysis of the Human Vascular Cell Adhesion Molecule 1 Promoter", *J. of Exp. Med.* 1992, 176, 1583–1593.

Shi, Y. and Hearst, "Thermostability of Double–Stranded Deoxyribonucleic Acids: Effects of Covalent Additions of a Psoralen", *Biochemistry* 1986, 25, 5895–5902.

Montgomery, K. et al., "Activation of Endothelial–Leukocyte Adhesion Molecule 1 (ELAM–1) Gene Transcription", *PNAS USA* 1991, 88, 6523–6527.

Gibbs, W., "State of Shock—Sepsis Can be Fatal to Firms as well as Patients", *Scientific American* 1994 Oct., 133–134.

\* cited by examiner

CHIMERIC OLIGONUCLEOTIDES FOR MODULATING GENE EXPRESSION

This is a division of application Ser. No. 08/147,878, filed Nov. 5, 1993 now U.S. Pat. No. 6,399,376.

FIELD OF THE INVENTION

The present invention is directed to the field of oligonucleotide therapeutic compositions and methods. Modulation, especially down-regulation, of genes or gene portions associated with disease states is a particular object of the invention. The invention provides therapeutic and research compositions which interact with certain transcriptional regulatory factors to modulate transcription of vascular cell adhesion molecule genes. Chimeric compositions having multi-modalities are also provided which can affect a plurality of gene functions by interfering with splicing or translation as well as transcription. Treatment of inflammatory and vascular diseases is a preferred embodiment of the present invention.

BACKGROUND OF THE INVENTION

Certain cellular adhesion molecules have been implicated in inflammatory and vascular diseases. As an example, a major mediator of the atherosclerotic process is the expression of specific adhesion molecule proteins on the surface of vascular endothelial cells. These adhesion molecules bind to immune cells, termed leukocytes, and initiate and propagate the inflammatory response that is likely central to both atherosclerosis and post-angioplasty restenosis. One of these vascular cell adhesion molecules, VCAM-1, plays an especially important role in atherosclerosis by binding a specific class of leukocytes, termed mononuclear leukocytes. Multiple signals induce the expression of VCAM-1. ICAM-1 and E-selectin are other inducible vascular cell adhesion molecules that mediate other aspects of general inflammatory response.

It is greatly desired to achieve palliative, diagnostic and therapeutic regimes for inflammatory disorders, atherosclerosis, restenosis and other diseases through modulation of the production of vascular cell adhesion molecules by cells. Specificity of such therapy is also greatly desired.

Oligonucleotides have recently become accepted as therapeutic moieties in the treatment of disease states in animals and man. For example, workers in the field have now identified antisense, triplex and other oligonucleotide therapeutic compositions which are capable of modulating expression of genes implicated in viral, fungal and metabolic diseases. For example, PCT patent applications PCT/US90/07067 filed Dec. 3, 1990; PCT/US91/01327 filed Feb. 25, 1991; and PCT/US91/05815 filed Aug. 14, 1991 disclose therapeutic oligonucleotides for treatment of papillomavirus, herpesvirus and cytomegalovirus infections respectively.

PCT patent application PCT/US91/05802 Filed Aug. 15, 1991 discloses oligonucleotides for treatment of Candida infections. PCT patent application US91/02628 filed Apr. 17, 1991 and PCT/US91/05209 filed Jul. 23, 1991 are directed to modulation of genes regulating lipid metabolism and cell adhesion respectively employing oligonucleotides as therapeutic agents. U.S. Ser. No. 007,997 filed Jan. 21, 1993 now U.S. Pat. No. 5,591,623, U.S. Ser. No. 063,167 filed May 17, 1993 now U.S. Pat. No. 5,514,788 and PCT patent application PCT/US93/08101 are also directed to oligonucleotide therapeutics relating to cellular adhesion molecules.

U.S. Pat. No. 5,098,890, in the name of Gewirtz, et al., is directed to antisense oligonucleotide therapies for certain cancerous conditions, while U.S. Pat. No. 5,166,195 issued Nov. 24, 1992 provides oligonucleotide inhibitors of HIV. It is, thus, established that oligonucleotides can be useful therapeutic instrumentalities and that the same can be configured to be useful in treatment regimes for treatment of cells and animals, especially humans.

It is apparent that oligonucleotide therapeutics is an accepted modality for treatment of disease. Methods of drug delivery and of modification to permit therapeutically significant residencies are now known. Notwithstanding the acceptance of oligonucleotide therapeutics, additional, effective approaches to gene modulation, especially down-regulation, employing oligonucleotides are greatly desired. Moreover, mechanisms of action for oligonucleotide therapeutics different from classical antisense and triplex mechanisms are also greatly desired.

Transcriptional regulatory factors (transcription factors) are DNA binding proteins which transduce extracellular signals into nuclear regulatory signals. Normally, transcriptional regulatory factors are activated or synthesized, translocate to the nucleus of cells, and bind to specific DNA sequences called enhancer or regulatory elements. Once bound, the transcriptional regulatory factor modulates gene transcription.

Wu, et al. "Inhibition of in Vitro Transcription by Specific Double-Stranded Oligodeoxy-ribonucleotides," Gene 89 203–209 (1990) used double stranded deoxyoligonucleotides to compete for binding of nuclear factors to specific promoter and enhancer elements. The authors tested the effect of oligonucleotide length, sequence and number of nuclear factor binding sites on in vitro transcription of adenovirus; potential therapeutic regimes were discussed. See also Holcenberg and Wu, WO 91/11535 which also discloses phosphorothioate derivatives in this context. Chu et al. "Binding of Hairpin and Dumbbell DNA to Transcription Factors" *Nucleic Acids Research* 19 6958 (1991) discloses the use of single stranded DNA in hairpin loop and ligated circular (dumbbell) forms for binding to transcription factors. See also Chu and Orgel, WO 92/18522.

Others have approached therapeutics through oligonucleotide interaction with transcription regulatory factors. Taniguchi, T. U.S. Pat. No. 5,157,115 issued Oct. 20, 1992 discloses nucleic acid compositions which inhibit or control the IL-2 or IL-2a genes by competitively binding to their respective transcription factors.

Blumenfeld et al. in WO 92/19732 and WO 91/15114 disclose antisense or sense oligonucleotides which can have a protein binding sequence.

Androphy et al. in European Patent Application 302,758 disclose nucleic acids or proteins for inhibiting the growth of a virus, such as papillomavirus, by preventing binding of a stimulatory protein encoded by the DNA of the virus (which protein would, if bound, enhance viral transcription) to the DNA of the virus. See also Androphy, et al, Nature 325:70–73 (1987) and Androphy et al., WO 91/14790, relating to inhibitors of transcription activation activity of papilloma viruses. Clusel, et al., Nucleic Acids Research 21:3405–3411 (1993) disclose ex vivo regulation of specific gene expression by nanomolar concentration of double-stranded dumbbell oligonucleotides containing a hepatic nuclear factor-1 binding site.

Bielinska, et al., Science 250:997–1000 (1990) regulated gene expression with double-stranded phosphorothioate oligonucleotides. Inhibition of sequence-specific DNA-binding proteins with oligonucleotides containing octamer or kB consensus sequences, which bound specifically either octamer transcription factor or NF-kB, were disclosed to inhibit HIV enhancer activation or IL-2 secretion.

Eck et al., Molecular and Cellular Biology 13:6530–6536 (1993), used high doses ($\geq 20$ μM) of a double-stranded 38 mer phosphorothioate oligonucleotide containing three tandem repeats of the NF-kB consensus binding sequence to inhibit the expression of both ICAM-1 and CD11b, a leukocyte integrin, in human endothelial cells in culture.

While interaction with transcriptional regulatory factors by DNA oligonucleotides has been known heretofore, and while therapies have been predicted to be possible, there have been no specific oligonucleotides and no effective methods using oligonucleotides for interaction with transcriptional regulatory factors which can effectively and specifically target vascular cell adhesion molecules, particularly VCAM-1, and diseases for which such molecules are implicated. Such materials and methods are greatly desired.

It is an object of the invention to provide oligonucleotide diagnostic and therapeutic compositions and methods for modulating expression of genes associated with disease states implicating vascular cell adhesion molecules, particularly VCAM-1.

A further object is to provide such oligonucleotides which interact with one or more transcription factors to effect such modulation.

Compositions and methods for treatment of inflammatory and vascular diseases as well as other disease states for which vascular cell adhesion molecules are implicated are also objects of the invention.

Yet another object is to afford oligonucleotide therapeutic compositions and treatment regimes which are directed to a plurality of gene portions in a multi-modal therapeutic approach.

Other objects will become apparent from review of the instant specification.

SUMMARY OF THE INVENTION

This invention relates to compositions and methods for modulating gene expression relating to vascular cell adhesion molecules. The expression of selected genes is modulated through interaction of novel oligonucleotides with a transcriptional regulatory factor appertaining to the gene. The invention is also directed to multimodal oligonucleotides and for methods for their employment for the modulation of preselected genes. Such multimodal oligonucleotides are capable of operating to downregulate or otherwise modulate such genes at a plurality of levels, such as splicing of pre-mRNA or translation of mRNA, preferably including interaction with at least one transcriptional regulatory factor.

The present invention also provides methods of diagnosis and therapy employing such oligonucleotides such that diseases or body states for which expression or overexpression of a gene coding for a vascular cell adhesion molecule are implicated can be diagnosed, palliated or cured through administration of oligonucleotides of the invention to cells or mammals, preferably humans.

In accordance with embodiments of this invention, methods for modulating expression of a gene coding for a vascular cell adhesion molecule are provided, which comprise selecting a portion of the gene. The gene is one which has a DNA sequence which binds a member of a family of transcriptional regulatory factors. Cells containing the gene are then contacted with an oligonucleotide moiety substantially identical in sequence to at least a portion of said binding sequence of the gene. The oligonucleotide moiety preferably comprises either two complementary strands of DNA or a single strand of DNA which is self-complementary.

In order that the oligonucleotide not be rapidly degraded by nucleases in the cells, it is preferred that the oligonucleotides be modified. Thus, modification of at least some of the inter-nucleotide linking groups, which are normally phosphodiesters is preferred. Phosphorothioate modifications, which are known per se to persons of skill in the nucleic acid art, are preferred. Other modifications to the linkages, and other modifications to the oligonucleotides, including sugar or base modifications, known to persons of skill in the art may also be employed.

While not wishing to be bound by theory, it is believed that modulation of expression of the gene in accordance with the present invention is effected through inhibition of transcription of the gene. This is believed to take place through interference with the normal effect of the transcriptional regulatory factor upon the gene.

It has been found to be possible to modulate genes which code for vascular cell adhesion molecules, particularly VCAM-1, ICAM-1 and E-selectin. In some embodiments, the transcriptional regulatory factor preferably is a member of the nuclear factor kB (NF-kB) family of transcriptional regulatory factors. Interference with other factors which also bind specific DNA sequences in the promotor region of vascular cell adhesion molecule genes is also believed to be effective in the practice of one or more aspects of the present invention. In preferred embodiments, these other factors include GATA, AP-1, Sp-1, AP-2, AP-3, interferon response factors, octamer transcription factor and NF-ELAM1. Specific DNA sequences include the ets binding sequence, TATA box, inverted CCAAT sequence, AP-1 binding site, NF-ELAM1 binding site, KR, KL, a CAT sequence, an Sp-1 binding site, AP-2 binding site, AP-3 binding site, interferon response element, octamer binding sequence and the GATA binding site.

In accordance with other aspects of the invention, oligonucleotide moieties are provided comprising a nucleotide sequence which is substantially identical to the sequence of at least a portion of a transcriptional regulatory factor binding sequence of a gene encoding a vascular cell adhesion molecule, particularly VCAM-1, ICAM-1 or E-selectin.

Multimodal oligonucleotides for modulation of gene expression are also contemplated by the present invention. Oligonucleotide moieties in accordance with these embodiments comprise a plurality of regions; i.e., they are chimeric. A first region has a sequence which is substantially identical to at least a portion of the sequence of a gene, which gene sequence binds a transcriptional regulatory factor. A second region of the oligonucleotide moiety is constructed to be specifically hybridizable either with mRNA deriving from the gene, or with a splicing region of pre-mRNA deriving from the gene. It is preferred that the first and second regions be capable of being liberated, one from the other, preferably in a cellular process, such that upon entry into cells, the chimeric oligonucleotides separate into several independent, effective subunits representing the first and second regions. This may be done by causing the first and second regions to flank a junction region in the oligonucleotide, which junction region is a substrate for a cellular metabolic process. For example, if the junction region is a substrate for RNAse H, upon entry into cells cleavage of the multimodal, chimeric oligonucleotides will liberate the first and second regions. To this end, it is preferred to stabilize the first and second regions against nuclease degradation and other forms of destruction such as by use of phosphorothioates, methyl phosphonates, peptide-nucleic acid (PNA) or other modified forms of nucleotides. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which are known to form two hydrogen bonds between them. "Specifically hybridizable" indicates a sufficient degree of complementarity to avoid non-specific binding of the oligonucleotide to non-target sequences. It is understood that an oligonucleotide need not be 100% complementary to its target nucleic acid sequence to be specifically hybridizable.

In accordance with other preferred embodiments, the chimeric oligonucleotides of the invention include at least a first and a second region, each having a DNA sequence substantially identical to a gene promotor region sequence which binds a different transcriptional regulatory factor, e.g. the regulatory factor which binds to the first region is different from the factor which binds to the second region. The first and second regions may be linked by stabilized internucleotide linkages such as phosphorothioate linkages. In other embodiments, the first and second regions are linked by a junction region which is a substrate for a cellular metabolic process, resulting in liberation of the first and second regions upon entry into cells.

In accordance with still other preferred embodiments, the chimeric oligonucleotides of the invention include three or more regions, at least one of which preferably has its sequence substantially identical to at least a portion of a transcriptional regulatory binding sequence on the gene to be modulated. The second, third, and other regions of the oligonucleotide may be the same or different and may comprise additional transcription factor binding sites or may be directed to interaction with splicing sites on pre-mRNA or to mRNA itself. It will be appreciated that the interaction of such oligonucleotide regions with pre-mRNA or mRNA is likely to occur in an antisense fashion, i.e., through specific hybridization with the mRNA or pre-mRNA.

Thus, the chimeric oligonucleotides of the invention may, in accordance with preferred embodiments, operate through distinctly different mechanisms. One mechanism can be an antisense mechanism directed towards pre-mRNA or mRNA while the other mechanism can be seen to scavenge transcriptional regulatory factor to prohibit such factor from interacting with genes to cause transcription thereof. The overall effect is to modulate expression of selected genes in a multi-modal fashion, that is, through operation of a plurality of different mechanisms. In accordance with other embodiments of the invention, methods for treating mammals, especially humans, which are suspected of having a disease involving expression of a selected gene are provided., Compositions including oligonucleotide moieties in accordance with the invention are administered to the mammal, usually in a pharmaceutically acceptable carrier or diluent and in accordance with therapeutic regimes, which effect palliation or cure of the disease. In accordance with one embodiment, inflammatory diseases can be treated such as atherosclerosis, restenosis and other inflammatory diseases in mammals, especially humans. In such case, one effective transcriptional regulatory factor for which interaction is preferred is a member of the NF-kB family of regulatory factors.

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature. Harlan, J. M., *Blood* 1985, 65, 513–525. In general, the first inflammatory cells to appear at the site of inflammation are neutrophils followed by mononuclear leukocytes, and lymphocytes. Cell-cell interactions are also critical for propagation of both B-lymphocytes and T-lymphocytes resulting in enhanced humoral and cellular immune responses, respectively.

The adhesion of white blood cells to vascular endothelium and other cell types is mediated by interactions between specific proteins, termed "adhesion molecules," located on the plasma membrane of both white blood cells and vascular endothelium. These vascular cell adhesion molecules bind to immune cells, termed leukocytes, and initiate and propagate the inflammatory response that is likely central to both atherosclerosis and post-angioplasty restenosis.

Vascular cell adhesion molecules are involved in the adherence of white blood cells to vascular endothelium and subsequent migration out of the vasculature. Vascular cell adhesion molecules identified to date include intercellular adhesion molecule 1 (ICAM-1), intercellular adhesion molecule 2 (ICAM-2), intercellular adhesion molecule 3 (ICAM-3), E-selectin [previously known as endothelial leukocyte adhesion molecule-1 (ELAM-1)], vascular cell adhesion molecule-1 (VCAM-1), L-selectin (MEL-14) and P-selectin (granule membrane protein-140, GMP-140) and their respective receptors. The adherence of white blood cells to vascular endothelium appears to be mediated in part if not in toto by ICAM-1, ICAM-2, E-selectin, VCAM-1 and P-selectin. Dustin and Springer, *J. Cell Biol.* 1987, 107, 321–331.

P-selectin and E-selectin are primarily involved in the adhesion of neutrophils to vascular endothelial cells. VCAM-1 primarily binds T and B lymphocytes. VCAM-1 plays an especially important role in atherosclerosis by binding a specific class of leukocytes, termed mononuclear leukocytes. In addition, VCAM-1 may play a role in the metastasis of melanoma, and possibly other cancers. ICAM-1 plays a role in adhesion of neutrophils to vascular endothelium, as well as adhesion of mononuclear leukocytes and lymphocytes to vascular endothelium, tissue fibroblasts and epidermal keratinocytes. ICAM-1 also plays a role in T-cell recognition of antigen presenting cell, lysis of target cells by natural killer cells, lymphocyte activation and proliferation, and maturation of T cells in the thymus. In addition, recent data have demonstrated that ICAM-1 is the cellular receptor for the major serotype of rhinovirus, which account for greater than 50% of common colds. Staunton et al., *Cell* 1989, 56, 849–853; Greve et al., *Cell* 1989, 56, 839–847.

Expression of ICAM-1, E-selectin and VCAM-1 has been associated with a variety of inflammatory skin disorders such as allergic contact dermatitis, fixed drug eruption, lichen planus, and psoriasis; Ho et al., *J. Am. Acad. Dermatol.* 1990, 22, 64–68; Griffiths and Nickoloff, *Am. J. Pathology* 1989, 135, 1045–1053; Lisby et al., *Br. J. Dermatol.* 1989,120, 479–484; Shiohara et al., *Arch. Dermatol.* 1989, 125, 1371–1376. In addition, ICAM-1, E-selectin and VCAM-1 expression has been detected in the synovium of patients with rheumatoid arthritis; Hale et al., *Arth. Rheum.* 1989, 32, 22–30; ICAM-1 expression has been detected in pancreatic B-cells in diabetes; Campbell et al., *Proc. Natl. Acad. Sci. U.S.A.* 1989, 86, 4282–4286; thyroid follicular cells in patients with Graves' disease; Weetman et al., *J. Endocrinol.* 1989, 122, 185–191; and expression of ICAM-1 and VCAM-1 has been associated with cardiac, renal and liver allograft rejection and in early atherosclerotic lesions.; Faull and Russ, *Transplantation* 1989, 48, 226–230; Adams et al., *Lancet* 1989, 1122–1125; O'Brien et al., *J. Clin. Invest.* 1993, 92, 945–951; Libby et al., *J. Clin. Invest.* 1993, 92, 538–539.

It has been hoped that inhibitors of ICAM-1, VCAM-1 and E-selectin expression would provide a novel therapeutic class of anti-inflammatory agents with activity towards a variety of inflammatory diseases or diseases with an inflammatory component such as asthma, rheumatoid arthritis, atherosclerosis and restenosis, allograft rejections, various dermatological conditions and psoriasis. In addition, inhibitors of ICAM-1, VCAM-1, and E-selectin may also be effective in the treatment of colds due to rhinovirus infection, AIDS, and some cancers and their metastasis. To date, there are no known therapeutic agents which effectively prevent the expression of the cellular adhesion molecules E-selectin, VCAM-1 and ICAM-1. The use of neutralizing monoclonal antibodies against adhesion molecules in animal models provide evidence that such inhibitors, if identified, would have therapeutic benefit for asthma; Wegner et al., *Science* 1990, 247, 456–459 and renal and cardiac allografts; Cosimi et al., *J. Immunol.* 1990, 144, 4604–4612. The use of a soluble form of ICAM-1 molecule was also effective in preventing rhinovirus infection of cells in culture. Marlin et al., *Nature* 1990, 344, 70–72.

Current agents which affect intercellular adhesion molecules include synthetic peptides, monoclonal antibodies, and soluble forms of the adhesion molecules. Monoclonal antibodies may prove to be useful for the treatment of acute inflammatory response due to expression of ICAM-1, VCAM-1 and E-selectin. However, with chronic treatment, the host animal develops antibodies against the monoclonal antibodies thereby limiting their usefulness. In addition, monoclonal antibodies are large proteins which may have difficulty in gaining access to the inflammatory site. Soluble forms of the cell adhesion molecules suffer from many of the same limitations as monoclonal antibodies in addition to the expense of their production. Thus, there is a long felt need for molecules which effectively inhibit vascular cell adhesion molecules. In particular, there is a long felt need for molecules which specifically inhibit VCAM-1, E-selectin and ICAM-1 expression. Therapeutic oligonucleotides can avoid many of the pitfalls of current agents used to block the effects of ICAM-1, VCAM-1 and E-selectin. This need has been partly satisfied through the use of antisense oligonucleotide interactions with mRNA coding for cellular adhesion molecules as reflected in patent applications owned by the assignee of this invention, referred to supra and incorporated herein by reference. There remains, however, a great need for further oligonucleotide therapeutics for cellular adhesion molecule-related body states and diseases.

Human ICAM-1 is encoded by a 3.3-kb mRNA resulting in the synthesis of a 55,219 Dalton protein the entirety of which is hereby incorporated by reference. ICAM-1 is heavily glycosylated through N-linked glycosylation sites. Staunton et al., *Cell* 1988, 52, 925–933. ICAM-1 is a member of the immunoglobulin supergene family, containing 5 immunoglobulin-like domains at the amino terminus, followed by a transmembrane domain and a cytoplasmic domain. The primary binding site for LFA-1 and rhinovirus are found in the first immunoglobulin-like domain. However, the binding sites appear to be distinct. Staunton et al., *Cell* 1990, 61, 243–354. ICAM-1 exhibits a broad tissue and cell distribution, and may be found on white blood cells, endothelial cells, fibroblast, keratinocytes and other epithelial cells. The expression of ICAM-1 can be regulated on vascular endothelial cells, fibroblasts, keratinocytes, astrocytes and several cell lines by treatment with bacterial lipopolysaccharide and cytokines such as interleukin-1, tumor necrosis factor, gamma-interferon, and lymphotoxin. See, e.g., Frohman et al., *J. Neuroimmunol.* 1989, 23, 117–124. The molecular mechanism for increased expression of ICAM-1 following cytokine treatment has not been well characterized.

E-selectin is a 115-Kda membrane glycoprotein which is a member of the selectin family of membrane glycoproteins. Bevilacqua et al., *Science* 1989, 243, 1160–1165 the entirety of which is hereby incorporated by reference. The amino terminal region of E-selectin contains sequences with homologies to members of lectin-like proteins, followed by a domain similar to epidermal growth factor, followed by six tandem 60-amino acid repeats similar to those found in complement receptors 1 and 2. These features are also shared by P-selectin and L-selectin antigen, a lymphocyte homing antigen. E-selectin is encoded for by a 3.9-kb mRNA. The 3'-untranslated region of E-selectin mRNA contains several sequence motifs ATTTA which are responsible for the rapid turnover of cellular mRNA consistent with the transient nature of E-selectin expression.

E-selectin exhibits a limited cellular distribution in that it has only been identified on vascular endothelial cells. Like ICAM-1, E-selectin is inducible by a number of cytokines including tumor necrosis factor, interleukin-1 and lymphotoxin and bacterial lipopolysaccharide. In contrast to ICAM-1, E-selectin is not induced by gamma-interferon. Bevilacqua et al., *Proc. Natl. Acad. Sci. USA* 1987, 84, 9238–9242; Wellicome et al., *J. Immunol.* 1990, 144, 2558–2565. The kinetics of E-selectin mRNA induction and disappearance in human umbilical vein endothelial cells precedes the appearance and disappearance of E-selectin on the cell surface.

VCAM-1 is a 110-Kda membrane glycoprotein encoded by a 3.2-kb mRNA. VCAM-1 appears to be encoded by a single-copy gene. Osborn et al., *Cell* 1989, 59, 1203–1211 the entirety of which is hereby incorporated by reference. Like ICAM-1, VCAM-1 is a member of the immunoglobulin supergene family, containing seven immunoglobulin-like domains of the H type. The receptor for VCAM-1 is proposed to be VLA4 integrin as demonstrated by the ability of monoclonal antibodies to VLA4 to block adherence of Ramos cells to VCAM-1. VCAM-1 is expressed on activated vascular endothelial cells and nonendothelial cells. Like ICAM-1 and E-selectin, expression of VCAM-1 on vascular endothelium is regulated by treatment with cytokines. Rice and Bevilacqua, *Science* 1989, 246, 1303–1306; Rice et al., *J. Exp. Med.* 1990, 171, 1369–1374. Increased expression appears to be due to induction of the mRNA.

Transcriptional regulatory factors, also known as transcription factors, the proteins which transduce extracellular signals into nuclear regulatory signals, are known per se and have been the subject of several reviews. For example, see Pabo, C. O. and Sauer, R. T., *Transcription factors: Structural Families and Principles of DNA Recognition* Annu. Rev. Biochem. 61:1053–1095 (1992); Morimoto, R. I., *Transcription Factors: Positive and Negative Regulators of Cell Growth and Disease,* Current Opinion in Cell Biology 4:480–487 (1992); and Hayashi, T., Ueno, Y., and Okamoto, T. *Oxidoreductive Regulation of Nuclear Factor kB,* J. Biol. Chem. 268:11380–11388 (1993), all of which are incorporated herein by reference to provide disclosure as to transcriptional regulatory factors, the nuclear factor kB (NF-kB) family and the interactions of the foregoing with nucleic acids.

NF-kB is an example of a family of eukaryotic transcriptional regulatory factors. NF-kB was discovered by Sen and Baltimore, Cell 1986, 46, 705–716, and was found to be a B cell-specific DNA binding protein that recognized a cis-regulatory element within the enhancer of the immunoglobulin gene. Subsequently, it has been shown that NF-kB is not restricted to B cells, but is inducible in a wide variety of cells. Latent NF-kB is a trimeric protein consisting of IkB, a cytosolic inhibitor of kB, and at least two distinct DNA binding proteins. Latent NF-kB becomes activated upon loss of IkB binding to dimeric NF-kB. IkB is an inhibitor of nuclear translocation for the DNA binding dimer. To date, at least three forms of DNA binding proteins have been identified which can form both homodimers and heterodimers, p50, p65 and rel. It is likely that other closely related gene products will be identified as well. Thus, NF-kB and proteins having similar structure or effect may be described as a family of proteins. Other examples of transcriptional regulatory factors are GATA, AP-1, Sp-1, AP-2, AP-3, interferon, octamer transcription factor and NF-ELAM1.

The promotor regions of the ICAM-1, E-selectin and VCAM-1 genes have been described, and all contain numerous regulatory elements. Of these, some have been well defined and others are putative transcription factor binding sites or consensus binding sequences.

Regulatory elements present in the 5' region of the human ICAM-1 gene include two TATA boxes located at bases −70 and −352 (i.e., 70 bases and 352 bases upstream or towards the 5' end of the translation initiation site) and a CAT-like sequence at −397. Computer analysis revealed two Sp-1 binding sites located at positions −246 and −99 and two sequences with homology to consensus AP-1/TRE binding sites at positions −1294 and −324. Voraberger et al., (1991) J. Immunol. 147:2777–2786; Degitz et al., (1991) J. Biol. Chem. 266:14024–14030. There are also sequences homologous to AP-2 binding sites at position −88 and an AP-3 like consensus binding site at position −414. A potential NF-kB binding site is found at position −540 and a potential interferon response element (IRE) is at position −109. The cis regulatory elements that are responsible, in part, for the cytokine responsiveness of the ICAM-1 gene are between position −300 and −1205. Cornelius et al., (1993) J. Invest. Dermatol. 100:753–758. Identified transcriptional regulatory factors that bind sequences in this region include NF-kB and AP-1. It is possible that additional DNA binding proteins interact with sequences in this region.

The E-selectin gene contains several consensus sequences for known DNA binding proteins. Located 97 bases upstream of the transcription initiation site is an inverted CCAAT consensus sequence (ATTGG; this promoter element is known to function in either orientation). A putative TATA box lies 30 bases upstream of the transcription initiation site. Collins et al., J. Biol. Chem.1991, 266, 2466–2473. A putative NF-kB binding element is present at position −94 and a putative AP-1 binding site is present at position −495. A DNA binding factor (NF-ELAM1) which recognizes DNA sequence in common with a T-cell enhancer is found at position −150 and in conjunction with the E-selectin NF-kB sequence was found to be sufficient to confer cytokine inducibility to a reporter gene construct transfected into endothelial cells. Hooft van Huijsduijnen et al., J. Biol. Chem., 1992, 267, 22385–22391.

A number of regulatory elements have been described on the VCAM-1 gene. A TATA box is found 29 bases upstream of the transcription initiation site. Two potential binding sites for NF-kB or NF-kB-like proteins are found at positions −63 and −77. Iademarco et al., 1992, J. Biol. Chem. 267, 16323–16329. A potential AP-1 binding site is found at position −495 and consensus ets binding sites are present at positions −221, −981 and −1033. GATA binding sequences are found at positions −245 and −259, and three potential octamer binding sites are found at positions −729, −1180 and −1554.

Multiple signals induce the expression of VCAM-1 including the cytokines TNFA, IL-1b and IL-4, bacterial lipopolysaccharide (LPS) and synthetic double-stranded oligonucleotides [poly (I:C)]. It is believed that these are mediated, at least in part, through a 36 base pair enhancer element, located between positions −75 and −35 of the human VCAM-1 gene, which contains the two adjacent KB-like binding sites, termed KL and KR. These elements are believed to bind two distinct transcriptional regulatory factors, both part of the NF-kB family of transcriptional regulatory factors.

A number of VCAM-1 gene regulatory elements, including the GATA, ets, KL and KR binding sites for transcription factors have now been identified. In the following sequence, the KL or "Left" binding site and the KR or "Right" binding site are underlined and labelled.

```
5'-TGGCTCTGCCCTGGGTTTCCCCTTGAAGGGATTTCCCTCCGCCTCT-3'  SEQ ID NO. 1

3'-ACCGAGACGGGACCCAAAGGGGAACTTCCCTAAAGGGAGGCGGAGA-5'
                LEFT (KL)    RIGHT (KR)
```

The KL and KR sites differ slightly in their sequences, and gel-shift experiments have shown that they appear to bind different transcription factors, both of which are believed to be members of the NF-KB family of transcriptional regulatory factors. Both sites are necessary, but neither is sufficient alone, for TNF stimulation of VCAM-1 expression. Each of the two binding sites shares characteristics with a different previously described site which binds a member of the NF-kB family. While not wishing to be bound by theory, it has been proposed that the distinct features of the two sites are responsible for the specificity of the VCAM-1 promotor. Iademarco et al.; *J. Biol. Chem.* 1992, 267, 16323–16329.

It can be seen that NF-kB-like and AP-1-like sites are shared by ICAM-1, VCAM-1 and E-selectin. Oligonucleotides incorporating one or both of these sequences are likely to affect transcription of all three vascular cell adhesion molecules. In contrast, oligonucleotides incorporating a regulatory element unique to a particular gene would be likely to have a specific effect on that gene. For example, GATA and octamer binding sequences are believed to be found in VCAM-1, but not ICAM-1 or E-selectin. Oligonucleotides incorporating one or more of these elements would be expected to inhibit VCAM-1 specifically. As other examples, oligonucleotides comprising the IRE sequence would be likely to differentially inhibit ICAM-1 and oligonucleotides comprising the NF-ELAM-1 sequence are likely to specifically inhibit E-selectin.

It is not necessary for the oligonucleotides to comprise the full length of the transcriptional regulatory factor binding site of the gene in order to be useful in modulating gene transcription. It is only necessary that the oligonucleotide therapeutic be substantially identical to a sufficient portion of the binding region or sequence of the gene as to effectively compete for binding of the transcriptional regulatory factor. Persons of ordinary skill in the art can easily ascertain optimal lengths of oligonucleotide for interaction with particular transcription factors.

It has also been found that single strands of nucleic acid can be used in accordance with this invention to modulate gene expression. Thus, a self-complementary unimolecular oligonucleotide sequence can "look like" double stranded DNA such that transcriptional regulatory factor can bind to it with concomitant down-regulation of the gene.

In certain embodiments, the two strands of a double-stranded oligonucleotide are covalently crosslinked to each other. Similarly, it may be desirable for a self-complementary oligonucleotide to be covalently crosslinked to stabilize the base-paired regions. Crosslinking of oligonucleotides is disclosed in PCT publication WO 93/18052, the contents of which are herein incorporated by reference.

For therapeutics, an animal suspected of having a disease which can be treated by decreasing the expression of ICAM-1, VCAM-1 and E-selectin is treated by administering oligonucleotides in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention employs oligonucleotides for use in inhibition of the expression of proteins capable of modulating inflammatory cell adhesion. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Modified bases and universal bases, particularly inosine, may also be used in the present invention.

The oligonucleotides in accordance with this invention preferably comprise from about 10 to about 80 nucleic acid base units. It is more preferred that such oligonucleotides comprise from about 12 to 50 nucleic acid base units, and still more preferred to have from about 18 to 35 nucleic acid base units. As will be appreciated, a nucleic acid base unit is a base-sugar combination suitably bound to an adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides is well within the talents of the routineer. It is also well known to use similar techniques to prepare other oligonucleotides such as the phosphorothioates and alkylated derivatives.

While the present invention has been described with specificity in accordance with certain of its preferred embodiments, the following examples serve only to illustrate the invention and are not intended to limit the same.

EXAMPLES

Example 1
Oligonucleotide Synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and phosphorothioate oligonucleotides were judged from electrophoresis to be greater than 80% full length material.

Example 2
Evaluation of Double-stranded Oligonucleotide Containing the VCAM-1 KF and KL Binding Sites on VCAM-1 and ICAM-1 Expression Interference with either the KL binding site or with the KR binding site or with both binding sites has been found to interfere with transcription of the gene, leading to diminished production of VCAM-1. The following double-stranded deoxyoligonucleotide, having phosphorothioate internucleotide linkages, was made through solid phase oligonucleotide synthesis of the individual strands:

```
SEQ ID NO. 2
5'-CTGCCCTGGGTTTCCCCTTGAAGGGATTTCCCTCCG-3'

3'-GACGGGACCCAAAGGGGAACTTCCCTAAAGGGAGGC-5'
              KL                KR
```

This oligonucleotide corresponds to the VCAM-1 promoter region (SEQ ID NO. 1) save for truncation of five nucleotides at each of the 5' and 3' ends. The KL and KR sites are underlined; the actual "native" KL and KR sites were used because it is believed that these mimic the natural regulatory elements more closely than consensus sequences.

Equal molar concentrations of the two strands were combined and heated to 65° C. for 5 minutes. The strands were allowed to anneal by slowly cooling to 25° C. The resulting double-stranded oligonucleotide was incubated with human microvascular endothelial cells (HMEC) for 15 hours at 37° C. VCAM-1 expression was induced by incubating cells with tumor necrosis factor (TNF-α, 100 u/ml) for 4 hours. Expression of VCAM-1 and ICAM-1, both of which contain binding sites for members of the NF-kB family of transcription factors, was determined by Northern blot analysis. The results shown in Table 1 demonstrate that double-stranded phosphorothioate VCAM-1 kB binding sites exhibit at least 100-fold selectivity for VCAM-1 compared to ICAM-1, the gene for which also contains a kB binding site. Thus is it believed that the kB binding site(s) on the VCAM-1 gene are distinct from the kB-binding site on the ICAM-1 gene.

TABLE 1

Inhibition of VCAM-1 expression by double-stranded phosphorothioate oligonucleotides

| ds Oligonucleotide Concentration (nM) | Relative Expression | |
| --- | --- | --- |
|  | VCAM-1 | ICAM-1 |
| 0 | 1.0 | 1.0 |
| 1 | 0.18 | 1.32 |
| 10 | 0.26 | 1.43 |
| 100 | 0.19 | 0.79 |
| 1000 | 0.12 | 0.40 |

Example 3
Evaluation of Double-stranded and Single-stranded (Self-complementary) Oligonucleotides Containing the VCAM-1 KF or KL Binding Site on VCAM-1 and ICAM-1 Expression The following phosphorothioate oligonucleotides were synthesized corresponding only to the left (KL) or right (KR) transcription factor binding sites of the promotor region of the VCAM-1 gene. The oligonucleotide for the left site comprised:
SEQ ID NO. 3
5'-GCCTGGGTTTCCCCTTGAA -3'
3'-CGGACCCAAAGGGGAACTT -5'
while the oligonucleotide for the right site comprised:
SEQ ID NO. 4
5'-TTGAAGGGATTTCCCTCCG -3'
3'-AACTTCCCTAAAGGGAGGC -5'

Preliminary data suggest that both SEQ ID NO: 3 and SEQ ID NO: 4 were capable of inhibiting VCAM-1 expression in endothelial cells and smooth muscle cells, showing even higher activity than the longer sequence (SEQ ID NO: 2). Thus, either full length or effective shorter portions of the gene sequence which binds the regulatory factor can be used for the sequence of the therapeutic oligonucleotides of the invention.

An additional oligonucleotide comprising the KL binding site with some additional complexity has the following sequence:
SEQ ID NO. 12
5'-GCCCTGGGTTTCCCCTTGAA -3'
3'-CGGGACCCAAAGGGGAACTT -5'

Self-complementary unimolecular oligonucleotide sequences can also be used. The following single stranded DNA oligonucleotides were constructed via solid phase synthesis. They were designed to have a sequence from the KL and KR sites of the VCAM-1 gene:

SEQ ID NO. 5 KL
5'-CTGGGTTTCCCTTTTCTCAGGGAAACCCAG -3'
SEQ ID NO. 6 KR
5'-GAAGGGATTTCCCTCTTCTTAGGGAAATCCCTTC -3'

An additional self-complementary DNA sequence with a phosphorothioate backbone having some less complexity was also synthesized based upon the left site of the binding region of the gene.
SEQ ID NO. 7 KL
5'-CTGGGTTTCCCCTTCAGGGAAACCCAG -3'

SEQ ID NO: 5 was heated to 65° and annealed by slow cooling as described above into its double-stranded (self-complementary form). 100 nM of oligonucleotide was incubated with confluent human primary umbilical cord endothelial cells (HUVEC) in 96 well plates for 18 hours at 37° C. TNF-α (100 u/ml) or LPS (100 ng/ml) was added to the cells and incubated another 18 hours. Cell surface VCAM-1 and ICAM-1 expression was determined by ELISA using VCAM-1 and ICAM-1 antibodies (R & D Systems, Minneapolis Minn.). The self-complementary phosphorothioate oligonucleotide containing part of the kB binding site for VCAM-1 selectively down-regulates VCAM-1 expression relative to ICAM-1 expression. This is shown in Table 2.

TABLE 2

Inhibition of VCAM-1 expression by self-complementary P=S oligonucleotide (100 nM) containing KL binding site

| | Absorbance | |
| Treatment | VCAM-1 | ICAM-1 |
| --- | --- | --- |
| Control | 0.008 ± 0.005 | 0.180 ± 0.025 |
| SEQ ID NO: 5 | 0 ± 0 | 0.109 ± 0.034 |
| TNF-α | 0.18 ± 0.132 | 0.383 ± 0.112 |
| TFN-α + SEQ ID NO: 5 | 0 ± 0.034 | 0.284 ± 0.024 |
| LPS | 0.322 ± 0.052 | 0.622 ± 0.008 |
| LPS + SEQ ID NO: 5 | 0 ± 0.007 | 0.509 ± 0.068 |

SEQ ID NO: 5 was also synthesized with a phosphodiester backbone and as a phosphorothioate with methoxy (2'-O-methyl) groups on the 2' position of the nucleotide sugars. These were compared to the phosphorothioate deoxy sequence. The oligonucleotides were heated to 65° C. and slowly cooled to allow strands to anneal. Oligonucleotides (100 nM) were incubated with HMEC in 96-well plates for 4 hours in the presence of 7 μg/ml DOTMA/DOPE mixture. TNF-α (100 u/ml) was added to the cells and incubated another 18 hours. Cell surface VCAM-1 and ICAM-1 expression was determined by ELISA using VCAM-1 and ICAM-1 antibodies. The results are shown in Table 3.

TABLE 3

Specific inhibition of VCAM-1 expression by 100 nM SEQ ID NO:5 (P = S)

| | Relative Expression | |
| Treatment | VCAM-1 | ICAM-1 |
| --- | --- | --- |
| TNF-α | 1.0 | 1.0 |
| TNF-α + SEQ ID NO: 5, P = S | 0.53 | 0.97 |
| TNF-α + SEQ ID NO: 5, P = S 2'-O—Me | 1.19 | 0.95 |
| TNF-α + SEQ ID NO: 5, P = O | 1.4 | 0.88 |
| Negative control DNA | 0.94 | 0.96 |

Example 4
Oligonucleotide Interference with VCAM Transcription

Competition for transcription factor binding: A protein was shown to be induced in TNF-α-treated HUVEC cells wich selectively bound to the VCAM-1 KL sequence. SEQ ID NO: 5 was shown by gel shift assay to compete with the natural KL sequence on the VCAM-1 gene for binding of this transcription regulatory protein.

CAT assays of VCAM-1 transcriptional activity after oligonucleotide treatment: A CAT reporter plasmid incorporating 288 nucleotides upstream of the VCAM-1 transcriptional start site fused in frame to the chloramphenicol acetyltransferase (CAT) gene was transfected into human HMEC cells in the presence or absence of SEQ ID NO: 5 or a mutated version of this oligonucleotide with an altered KL binding region, using standard calcium phosphate transfection techniques. Cells were treated with TNF-α (100 u/ml) for approximately 48 hours and cytosolic extracts were prepared, CAT activity was determined by thin layer chromatography and expressed as percent conversion of chloramphenicol to its acetylated form. Results are shown in Table 4:

TABLE 4

| Oligonucleotide effect on VCAM transcription | |
| --- | --- |
| Neg control | 0.65 |
| TNF-α | 1.16 |
| TNF + SEQ ID NO: 5 | 0.67 |
| TNF + mut. SEQ ID NO: 5 | 2.11 |

These results suggest that SEQ ID NO: 5 inhibits the induction of VCAM-1 transcription by TNF-α.

Example 5
Effect of Chimeric Multimodal Oligonucleotide on VCAM-1, ICAM-1 and E-selectin Expression An exemplary chimeric oligonucleotide was also prepared having multi-modality. A first region of the chimeric oligonucleotide is double-stranded DNA having a sequence from the left site of the VCAM-1 coding gene which binds transcriptional regulatory factor. A second region of the oligonucleotide comprises a DNA having a sequence known to one of the inventors to have significant, traditional antisense activity against VCAM-1. See PCT Patent Application No. PCT/US91/05209 filed Jul. 23, 1991, and U.S. Ser. No. 007,997 filed Jan. 21, 1993, the entirety of which is incorporated herein by reference. The two regions of the oligonucleotide are joined together by a junction region. The following oligonucleotide (SEQ ID NO: 8) was made; bold type denotes the double stranded phosphorothioate DNA which binds the transcriptional regulatory factor, the underlined portion connotes phosphorothioate DNA having the sequence for antisense interaction with VCAM-1 mRNA and the normal type shows either DNA or RNA which is either a junction region or therapeutically ineffective sequence included for stability.
SEQ ID NO. 8
5'-GCCTGGGTTTCCCCCTTGAATTTGCACTGTGTCT CCTGTCTCCGCT -3'
3'-CGGACCCAAAGGGGAACTTAAACGTGACACAG AGGACAGAGGCGA -5'

In this embodiment, the double stranded regulatory factor binding region (bold type) and the antisense strand of the region (underlined) were synthesized to have phosphorothioate backbones. The remaining nucleotides, including the junction region and the sense strand of the antisense region, had wild-type, phosphodiester internucleotide linkages. This multimodal oligonucleotide was evaluated in a preliminary experiment to compare effects of 10 nM oligonucleotides on TNF-α-induced VCAM-1 expression in HUVEC cells.

The oligonucleotides were heated to 65° C. and slowly cooled to allow strands to anneal. 10 nM of oligonucleotide [multimodal (SEQ ID NO: 8), self-complementary unimolecular (SEQ ID NO: 5) and a mutated version of SEQ ID NO: 5 having a mutated KL site] and 7 μl/ml lipofectin was added to OPTIMEAM washed confluent, early passaged primary HUVE cells in 96-well plates. After 5 hours, the wells were washed and 20% FCS/DMEM was added for two hours. 100 u/ml TNF-α was then added. After an additional 18 hours, cell surface expression of VCAM-1 or ICAM-1 was determined by ELISA assay on live cells using commercially available antibodies to ICAM-1 and VCAM-1. The results shown in Table 5 are the mean of triplicate assays for each point.

TABLE 5

Effect of unimolecular and multimodal oligonucleotides (10 nM) on VCAM-1 and ICAM-1 expression

|  | VCAM-1 | ICAM-1 |
| --- | --- | --- |
| TNF | 0.167 | 0.252 |
| TNF + SEQ ID NO: 5 | 0.168 | 0.236 |
| TNF + SEQ ID NO: 8 | 0.136 | 0.28 |
| TNF + mut. SEQ ID NO: 5 | 0.168 | 0.24 |
| Negative control | 0.005 | 0.179 |

This preliminary experiment demonstrated that, at an extremely low oligonucleotide concentration at which the self-complementary oligonucleotide (SEQ ID NO: 5) comprising the VCAM-1 transcription factor KL binding site did not inhibit VCAM-1 expression, the multimodal oligonucleotide containing both the KL site and an antisense region targeted to VCAM-1 (SEQ ID NO: 8) inhibited VCAM-1 expression by approximately 27%. This suggests that the multimodal oligonucleotide may be even more effective than the oligonucleotide comprising only the transcription factor binding site.

Example 6
Oligonucleotides Containing Other VCAM-1 Regulatory Sequences

A double-stranded oligonucleotide containing the GATA sequence element from human VCAM-1 was synthesized as a phosphorothiate. The sequence is as follows:
TTTATCTTTCCAGTAAAGATAGCCTTTTGGA (SEQ ID NO: 9)
AAATAGAAAGGTCATTTCTATCGGAAAACCT A unimolecular self-complementary oligonucleotide containing the same GATA sequence was also synthesized:
CTATCTTTCCAGTAAAGATAGTTC-TATCTTTACTCGAAAGATAG (SEQ ID NO: 10)

A double-stranded oligonucleotide containing the proximal ets sequence from human VCAM-1 was also synthesized:
GTCGAAGATGAGGAAAGCCTGTATTTTATA (SEQ ID NO: 11)
CAGCTTCTACTCCTTTCGGACATAAAAATAT These oligonucleotides were tested under optimized conditions (same as previous example except HUVE cells were 75% confluent) and the results are expressed in Table 6 as percent inhibition of expression after TNF-α induction.

TABLE 6

Effect of regulatory sequence oligonucleotides on vascular adhesion molecule expression
(Expressed as percent inhibition compared to expression without oligo, after TNF-α treatment)

|  | VCAM-1 | E-selectin | ICAM-1 |
| --- | --- | --- | --- |
| 100 nM KL (SEQ ID NO: 5) | 94.26 | 106.85 | 37.01 |
| 10 nM KL (SEQ ID NO: 5) | 77.05 | −23.97 | 12.20 |
| 1 nM KL (SEQ ID NO: 5) | 57.38 | 5.48 | 7.48 |
| 100 nM ds GATA (SEQ ID NO: 9) | 71.31 | 23.29 | 5.51 |
| 10 nM ds GATA (SEQ ID NO: 9) | 94.26 | 15.75 | 35.24 |
| 100 nM GATA (SEQ ID NO: 10) | 93.44 | 20.55 | −2.56 |
| 10 nM GATA (SEQ ID NO: 10) | 81.97 | 39.04 | −9.08 |
| 100 nM ets (SEQ ID NO: 11) | 81.15 | 22.60 | 36.81 |
| 10 nM ets (SEQ ID NO: 11) | 88.52 | 30.82 | 13.98 |

Also in this experiment, SEQ ID NO: 5 was tested at concentrations between 1 nM and 100 nM for ability to inhibit VCAM-1, ICAM-1 and E-selectin expression under optimized conditions. The results are also shown in Table 6. These data indicate that at 100 nM, SEQ ID NO: 5 completely blocks both VCAM-1 and E-selectin induction with only a 37% inhibition of ICAM-1. At lower concentrations, VCAM-1 is still blocked by greater than 50% but there is no effect on either E-selectin or ICAM-1.

At all concentrations of either the bimolecular ets or GATA oligonucleotides or the unimolecular self-complementary GATA oligonucleotide, VCAM-1 expression was inhibited by greater than 70% with zero to 40% inhibition of either E-selectin or ICAM-1.

Oligonucleotides containing "native" VCAM-1 enhancer elements are thus able to regulate VCAM-1 expression with a specificity and selectivity which would not be expected with, for example, oligonucleotides containing a consensus regulatory sequence.

What is claimed is:

1. A linear chimeric oligonucleotide for down-regulating expression of a gene comprising a first region having a sequence which is identical to at least a portion of a sequence of said gene, which gene sequence binds a transcriptional regulatory factor, and a second region specifically hybridizable either with a splicing region of pre-mRNA deriving from the gene or with mRNA deriving from the gene.

2. The chimeric oligonucleotide of claim 1 wherein said first and second regions are stabilized against nuclease degradation.

3. The chimeric oligonucleotide of claim 1 wherein said first and second regions flank a junction region which is a substrate for a cellular nuclease.

4. The chimeric oligonucleotide of claim 3 wherein said cellular nuclease is RNAse H or DNAse.

5. The chimeric oligonucleotide of claim 2 wherein said first and second regions flank a junction region which is a substrate for a cellular nuclease and the first and second regions are stabilized against nuclease degradation.

6. The chimeric oligonucleotide of claim 5 wherein said cellular nuclease is RNAse H or DNAse.

7. The chimeric oligonucleotide of claim 5 wherein said first and second regions are stabilized by phosphorothioate linking groups between nucleotide units of the region.

8. A linear chimeric oligonucleotide for down-regulating expression of a gene comprising a first region having a sequence which is identical to at least a portion of a sequence of a gene, which gene sequence binds a transcriptional regulatory factor, a second region specifically hybridizable with a splicing region of pre-mRNA deriving from the gene, and a third region specifically hybridizable with mRNA deriving from the gene.

9. The chimeric oligonucleotide of claim 8 wherein each of said first, second, and third regions is stabilized against metabolic degradation and flank junction regions which are labile to metabolic degradation.

\* \* \* \* \*

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 46
      (B) TYPE: Nucleic Acid
      (C) STRANDEDNESS: Double
      (D) TOPOLOGY: Linear (iv) ANTI-SENSE: No (xi) SEQUENCE DESCRIPTION: SEQ ID NO: 1:

TGGCTCTGCC CTGGGTTTCC CCTTGAAGGG ATTTCCCTCC GCCTCT                    46

(2) INFORMATION FOR SEQ ID NO: 2:

(i) SEQUENCE CHARACTERISTICS:
            (A) LENGTH: 36
            (B) TYPE: Nucleic Acid
            (C) STRANDEDNESS: Double
            (D) TOPOLOGY: Linear (iv) ANTI-SENSE: No (xi) SEQUENCE DESCRIPTION: SEQ ID NO: 2:

CTGCCCTGGG TTTCCCCTTG AAGGGATTTC CCTCCG                                36

(2) INFORMATION FOR SEQ ID NO: 3:

(i) SEQUENCE CHARACTERISTICS:
            (A) LENGTH: 19
            (B) TYPE: Nucleic Acid
            (C) STRANDEDNESS: Double
            (D) TOPOLOGY: Linear (iv) ANTI-SENSE: No (xi) SEQUENCE DESCRIPTION: SEQ ID NO: 3:

GCCTGGGTTT CCCCTTGAA                                                  19

(2) INFORMATION FOR SEQ ID NO: 4:

(i) SEQUENCE CHARACTERISTICS:
            (A) LENGTH: 19
            (B) TYPE: Nucleic Acid
            (C) STRANDEDNESS: Double
            (D) TOPOLOGY: Linear (iv) ANTI-SENSE: No (xi) SEQUENCE DESCRIPTION: SEQ ID NO: 4:

TTGAAGGGAT TTCCCTCCG                                                  19

(2) INFORMATION FOR SEQ ID NO: 5:

(i) SEQUENCE CHARACTERISTICS:
            (A) LENGTH: 30
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 5:

CTGGGTTTCC CTTTTCTCAG GGAAACCCAG                                      30

(2) INFORMATION FOR SEQ ID NO: 6:

(i) SEQUENCE CHARACTERISTICS:
            (A) LENGTH: 34
            (B) TYPE: Nucleic Acid
            (C) STRANDEDNESS: Single
            (D) TOPOLOGY: Linear (iv) ANTI-SENSE: No (xi) SEQUENCE DESCRIPTION: SEQ ID NO: 6:

GAAGGGATTT CCCTCTTCTT AGGGAAATCC CTTC                    34

(2) INFORMATION FOR SEQ ID NO: 7:

(i) SEQUENCE CHARACTERISTICS:
        (A) LENGTH: 27
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 7:

CTGGGTTTCC CCTTCAGGGA AACCCAG                            27

(2) INFORMATION FOR SEQ ID NO: 8:

(i) SEQUENCE CHARACTERISTICS:
        (A) LENGTH: 45
        (B) TYPE: Nucleic Acid
        (C) STRANDEDNESS: Double
        (D) TOPOLOGY: Linear (iv) ANTI-SENSE: Yes (xi) SEQUENCE DESCRIPTION: SEQ ID NO: 8:

GCCTGGGTTT CCCCTTGAAT TTGCACTGTG TCTCCTGTCT CCGCT        45

(2) INFORMATION FOR SEQ ID NO: 9:

(i) SEQUENCE CHARACTERISTICS:
        (A) LENGTH: 31
        (B) TYPE: Nucleic Acid
        (C) STRANDEDNESS: Double
        (D) TOPOLOGY: Linear (iv) ANTI-SENSE: No (xi) SEQUENCE DESCRIPTION: SEQ ID NO: 9:

CTTTC CAGTAAAGAT AGCCTTTTGG A                            31

(2) INFORMATION FOR SEQ ID NO: 10:

(i) SEQUENCE CHARACTERISTICS:
        (A) LENGTH: 44
        (B) TYPE: Nucleic Acid
        (C) STRANDEDNESS: Single
        (D) TOPOLOGY: Linear (iv) ANTI-SENSE: <Unknown>

(xi) SEQUENCE DESCRIPTION: SEQ ID NO: 10:

TTTCC AGTAAAGATA GTTCTATCTT TACTCGAAAG ATAG              44

(2) INFORMATION FOR SEQ ID NO: 11:

(i) SEQUENCE CHARACTERISTICS:
        (A) LENGTH: 31
        (B) TYPE: Nucleic Acid
        (C) STRANDEDNESS: Double
        (D) TOPOLOGY: Linear (iv) ANTI-SENSE: <Unknown>

(xi) SEQUENCE DESCRIPTION: SEQ ID NO: 11:

AGATG AGGAAAGCCT GTATTTTTAT A                            31

(2) INFORMATION FOR SEQ ID NO: 12:

(i) SEQUENCE CHARACTERISTICS:
        (A) LENGTH: 20
        (B) TYPE: Nucleic Acid
        (C) STRANDEDNESS: Double
        (D) TOPOLOGY: Linear (iv) ANTI-SENSE: No (xi) SEQUENCE DESCRIPTION: SEQ ID NO: 12:

GCCCTGGGTT TCCCCTTGAA                                          20